United States Patent [19]

Hunter

[11] Patent Number: 4,574,000
[45] Date of Patent: Mar. 4, 1986

[54] ARTIFICIAL FALLOPIAN TUBE

[76] Inventor: Stephen K. Hunter, 1402 S. 1025 West, Syracuse, Utah 84041

[21] Appl. No.: 644,315

[22] Filed: Aug. 24, 1984

[51] Int. Cl.$^4$ .................. A61F 2/04; A61M 25/00
[52] U.S. Cl. .................................. 623/12; 128/1 R; 604/8; 604/55
[58] Field of Search .................. 3/1; 604/8, 55; 128/1 R

[56] References Cited

U.S. PATENT DOCUMENTS

| Re. 29,207 | 5/1977 | Bolduc et al. | 128/1 R X |
| 4,326,505 | 4/1982 | Cropsey | 128/1 R |
| 4,531,933 | 7/1985 | Norton et al. | 604/8 |

OTHER PUBLICATIONS

Carl Wood et al., *Fertility and Sterility* 22: 446-450 (Jul. 1979) "A Preliminary Design and Trial of an Artificial Human Tube".
Bjorn A. Afzelius et al., *Fertility and Sterility* 29: 72-74 (Jan. 1978) "On The Function of Cilia in the Female Reproductive Tract".
Peter McComb et al., *Fertility and Sterility* 31: 673-676 (Jun. 1979) "The Influence of Fallopian Tube Length on Fertility in the Rabbit".
Trudy Trimbos-Kemper et al., *Fertility and Sterility* 37: 384-388 (Mar. 1982) "Etiological Factors in Tubal Infertility".
Victor Gomel, *Fertility and Sterility* 39: 144-156 (Feb. 1983) "An Odyssey Through the Oviduct".
Clifford Grobstein et al., *Science* 222: 127-132 (Oct. 1983) "External Human Fertilization: An Evaluation of Policy".
Brochure dated 1983 entitled, "Human Reproduction and Technology: Legal and Ethical Dilemmas", prepared by the Medical College of Wisconsin.
Carl J. Pauerstein et al., "The Anatomy and Physiology of the Oviduct", review course excerpts.

*Primary Examiner*—Richard J. Apley
*Assistant Examiner*—Alan W. Cannon
*Attorney, Agent, or Firm*—Workman, Nydegger & Jensen

[57] ABSTRACT

The present invention is directed to methods and apparatus for artificially transporting an egg from an ovary to the uterus in a patient having dysfunctional natural fallopian tubes. A preferred embodiment of the apparatus of the present invention includes an ovisac in which one of the patient's ovaries is encapsulated in order to collect any ova discharged. A plurality of fluid supply tubes serve to wash the ova toward a tubular member that is secured in communication with the uterine cavity. In one embodiment, a reservoir of fluid and a programmable micropump are provided, both of which are adapted to be implanted in the patient. The method of the present invention advantageously comprises the initial step of charging the artificial fallopian tube with a solution of nutrients and sperm immediately prior to ovulation. After fertilization has had an opportunity to occur, nutrient solution is introduced into the fallopian tube in a continuous, but pulsatile manner at a rate that will cause the ovum to be ejected into the uterine cavity about two to three days after ovulation.

23 Claims, 6 Drawing Figures

ARTIFICIAL FALLOPIAN TUBE

BACKGROUND

1. Field of the Invention

The present invention relates to methods and apparatus utilized in artificial fertilization. More particularly, the present invention is directed to an artificial fallopian tube and methods for artificially transporting an egg from an ovary to the uterus.

2. The Prior Art

A surprisingly large number of married couples are unable to have children due to problems of infertility. In the United States alone, it is estimated that about one out of every six to seven marriages are affected.

Of the various causes for infertility, the most common problem is related to dysfunction of the fallopian tubes (sometimes also referred to as the "oviducts"), the incidence of tubal infertility comprising about thirty to forty percent of all causes of infertility. In the United States, this translates to about 500,000 American women that are unable to have children due to some dysfunction of their fallopian tubes.

The traditional solution to the problem of tubal dysfunction has been adoption. Unfortunately, due to the increasing availability and use of contraceptives and also the legalization and widespread practice of abortion, the number of healthy infants available for adoption relative to the number of couples seeking to adopt has substantially decreased in recent years. Adoption is simply not available to every couple that wishes to have a child.

Since tubal dysfunction is the major cause of infertility, researchers have long attempted to develop techniques for restoring normal tubal function to dysfunctional fallopian tubes. Surgeons have tried to repair damaged fallopian tubes, have tried transplanting healthy fallopian tubes from a donor, and have tried other surgical techniques to reconstruct or repair damaged tubes. Unfortunately, these efforts have proved largely ineffective.

Largely because of the disappointing failures of traditional surgical techniques, researchers eventually looked to means for totally bypassing damaged fallopian tubes. The technology of "in vitro fertilization" (resulting in what are often termed "test tube babies") circumvents dysfunctional oviducts through a delicate procedure involving surgically removing a mature egg (an "ova") immediately prior to ovulation and placing it into a nutrient medium containing sperm. After fertilization, the embryo is nurtured during a number of cell divisions and then surgically placed into the uterine cavity for development.

Although more effective than earlier approaches to the problem of infertility, the practice of in vitro fertilization suffers from some serious disadvantages.

First, the practice of in vitro fertilization is extremely expensive, even in those cases that prove unsuccessful. It was estimated that costs of nearly $40,000 were required in 1983 to ensure a roughly fifty percent chance of a live birth in a particular patient. This high cost is prohibitive for many couples, particularly if more than one child is desired.

Less tangible, but potentially much more important are ethical concerns relating to the practice of in vitro fertilization. One problem that has been acknowledged is that a large number of embryos die due to imperfections and limitations of the in vitro fertilization process. Other concerns are that the in vitro technique will be utilized to effect embryo manipulation, or that in vitro techniques might induce congenital abnormalities in those born as a result of the technique. Many legal issues are raised by the practice of in vitro fertilization. Despite these important concerns, the failure of modern medicine to offer other practical alternatives to those couples who want children has led to general acceptance of the in vitro fertilization technique.

In view of the foregoing, it will be appreciated that it would be a significant advancement in the treatment of infertility if new methods and apparatus could be provided that were capable of effectively treating patients suffering from tubal dysfunction without the problems inherent in the use of in vitro techniques. It would also be a significant advancement if methods and apparatus for artificially assisting the induction of pregnancy could be provided that did not require multiple surgical operations. Such methods and apparatus are disclosed and claimed herein.

BRIEF SUMMARY AND OBJECTS OF THE INVENTION

The present invention is directed to novel methods and apparatus for restoring fertility to women suffering from dysfunctional fallopian tubes.

A preferred embodiment of the apparatus of the present invention comprises an ovisac in which one of the patient's ovaries is encapsulated so as to collect ova discharged during ovulation. A plurality of fluid supply tubes are secured in communication with the ovisac in a manner that will wash ova toward a tubular member secured in communication with the patient's uterine cavity.

In one embodiment, the apparatus of the present invention further includes an implantable programmable micropump and an implantable fluid reservoir. In another embodiment the pump and fluid supply source are supplied externally, being secured to an injection member extending from the patient's abdomen.

The method of the present invention includes the step of initially charging an artificial fallopian tube with a solution of nutrients and sperm shortly prior to ovulation. After fertilization, nutrient solution is introduced in a continuous pulsatile manner at a rate that will cause the ovum to be ejected into the patient's uterine cavity at a time when nidation is possible, generally two to three days after ovulation.

It is, therefore, a primary object of the present invention to provide an artificial fallopian tube, and method of artificially collecting and fertilizing an ovum and introducing the fertilized ovum into the uterus of a patient having dysfunctional fallopian tubes.

It is another object of the present invention to provide methods and apparatus that are capable of use without substantial expense or inconvenience in connection for use with a patient having dysfunctional fallopian tubes that wishes to have one or more children.

These and other objects and features of the present invention will become more fully apparent from the following description and appended claims taken in conjunction with the accompanying drawings.

BRIEF DESCRIPTION OF THE DRAWINGS

In the accompanying drawings, which represent the best mode presently contemplated for carrying out the invention.

DETAILED DESCRIPTION OF THE INVENTION

Figure 1:
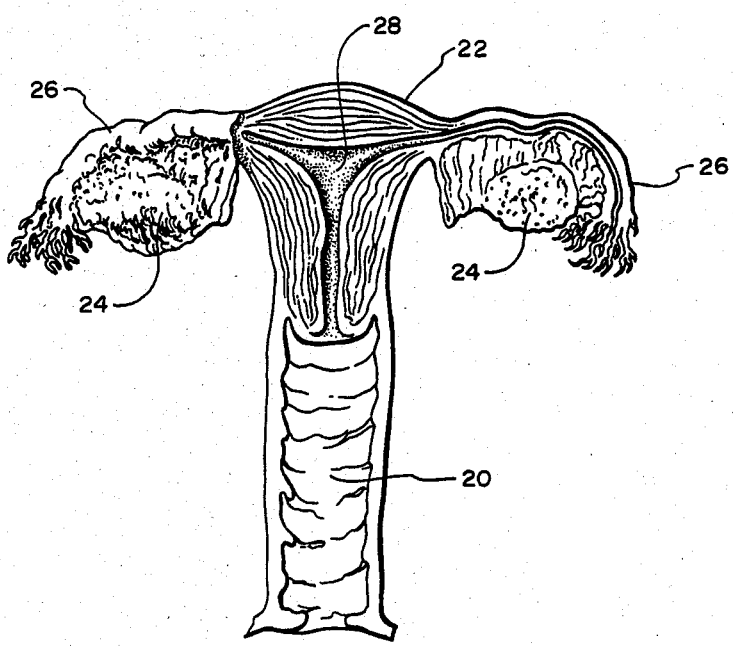
FIG. 1 is a front view of the human female sex organs, a portion being broken away for convenience of illustration.

The present invention can best be understood in the context of the relationship and general function of the various female sexual organs. FIG. 1 illustrates these female sexual organs, including the vagina 20, the uterus 22, the ovaries 24, and the fallopian tubes 26.

Reproduction begins with development of ova (eggs) in the ovaries. At the middle of each monthly sexual cycle a single ovum is expelled from one of the ovaries and is collected by the associated fallopian tube. This ovum then passes through the fallopian tube into the uterine cavity 28, where, if it has been fertilized, it implants onto the uterine wall and develops into a fetus.

Figure 2:
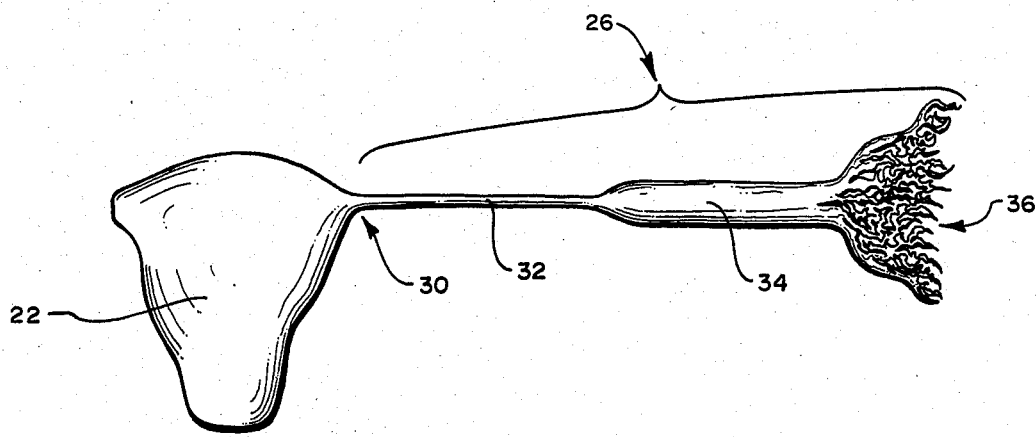
FIG. 2 is a diagrammatic representation of a human fallopian tube.

FIG. 2 is a representation of a fallopian tube. A human fallopian tube is about four inches long. In FIG. 2 it may be seen that fallopian tubes 26 are comprised of a junction 30, known as the "utero-tubal junction", a capillary-like passage known as the "isthmus" 32, a somewhat broader passageway termed the "ampulla" 34, and an opening known as the "infundibulum" 36. The infundibulum is provided with a number of finger-like projections termed "fimbria" that aid in collecting the ovum from the ovaries. The interior surfaces of the fallopian tube are lined with mucosal cells.

A fallopian tube is an extremely complex organ. Its operation is controlled by the presence of particular ovarian hormones that may be present from time to time during the sexual cycle.

At the time of ovulation, the fimbria of the infundibulum become fringed, fluted, and lanciform. Muscular contractions cause the fimbria to be displaced from their normal position so as to almost completely surround the ovary. More than half of the mucosal cells which line the infundibulum are ciliated cells. The cilia of these cells establish a current capable of drawing an ovulated egg into the ampulla.

The interior of the ampulla 34 is completely filled with mucosal tissue formed in a complex pattern of folds. These folds separate as the egg is moved through the ampulla. Again, somewhat in excess of half of the mucosal cells lining the passageway are ciliated and beat toward the uterus.

Of the hundred of millions of spermatozoa that are deposited in the vagina during sexual intercourse, only a few reach the proximal ampulla, where fertilization occurs. The fertilized egg then continues to travel by ciliary motion through the ampulla, and then through the isthmus by means of peristaltic muscular contractions. After about five to seven days, the fertilized egg is expelled into the uterine cavity. Due to hormonal changes that occur following ovulation, the uterine cavity becomes prepared for the arrival of the egg so that a fertilized egg will become implanted (through a process called "nidation") onto the uterine wall where it will develop into a fetus.

The present invention does not attempt to emulate every aspect of this very complex organ. Rather, the present invention is designed to satisfy the following general requirements: (1) the artificial fallopian tube must provide a favorable environment in which fertilization can take place; (2) the ovum, sperm and the fertilized egg must be maintained in a viable condition while in the artificial fallopian tube; and (3) the fertilized ovum must be ejected into the uterine cavity at a time when nidation is possible.

Figure 3:
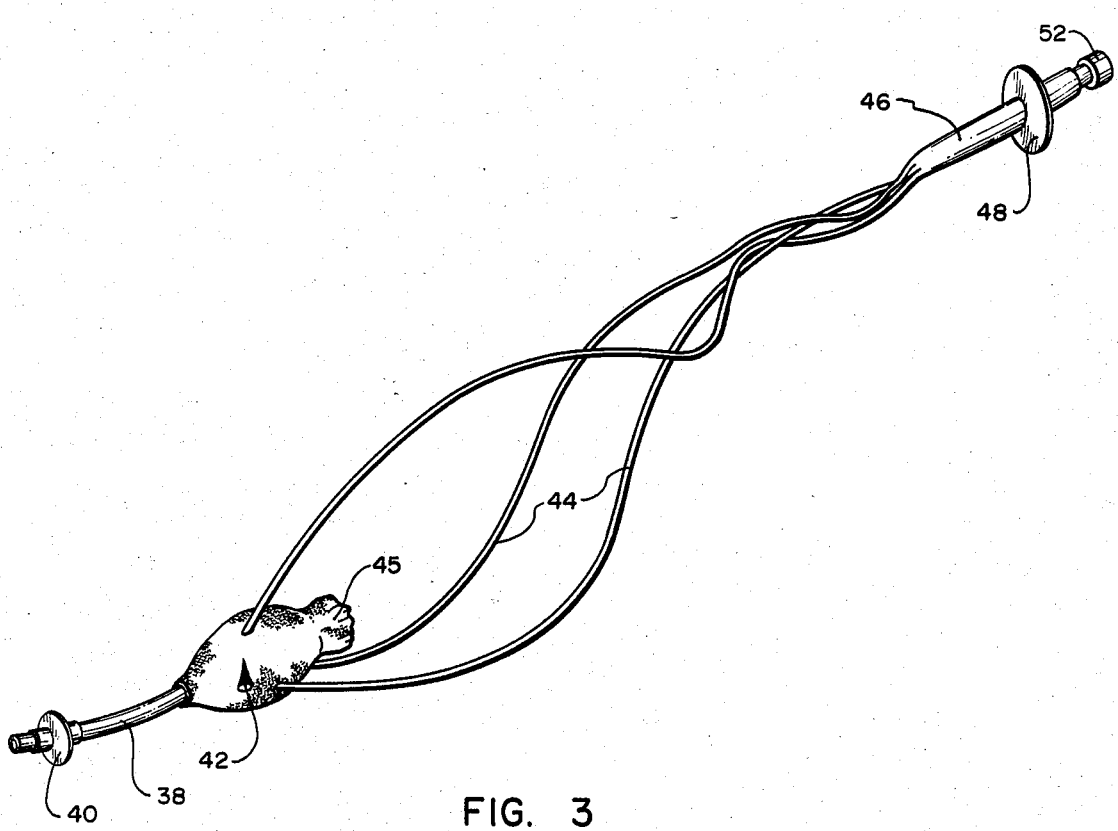
FIG. 3 is a perspective view of a presently preferred embodiment of an artificial fallopian tube according to the present invention.
Figure 4:
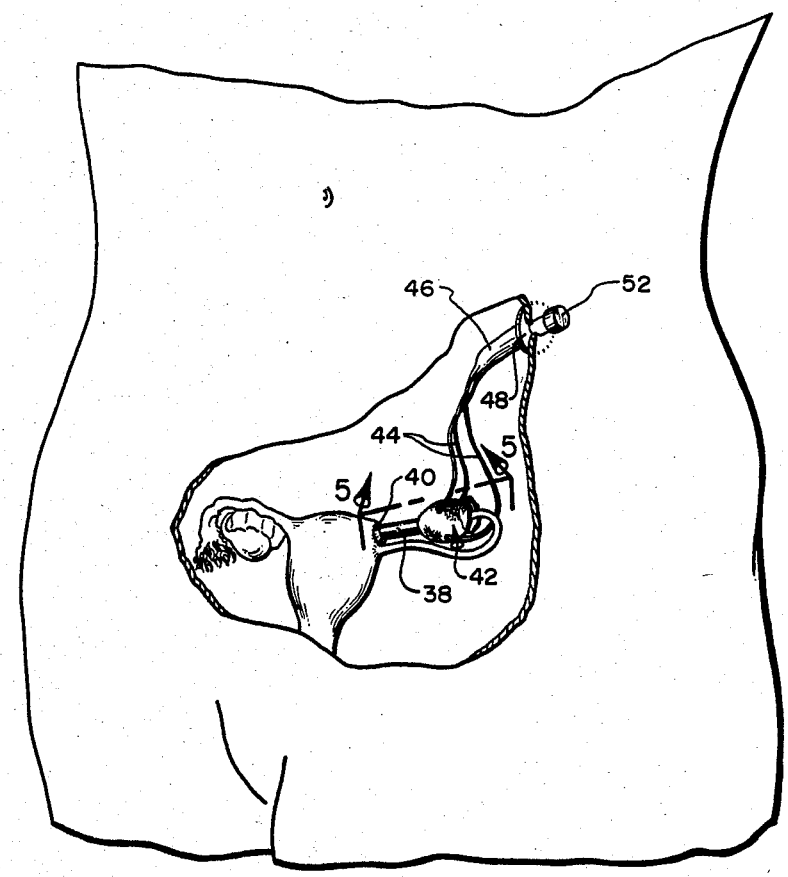
FIG. 4 is a fragmentary view of a human female into which the embodiment illustrated in FIG. 3 has been surgically implanted, with portions of the abdominal wall being broken away for convenience of illustration.
Figure 5:
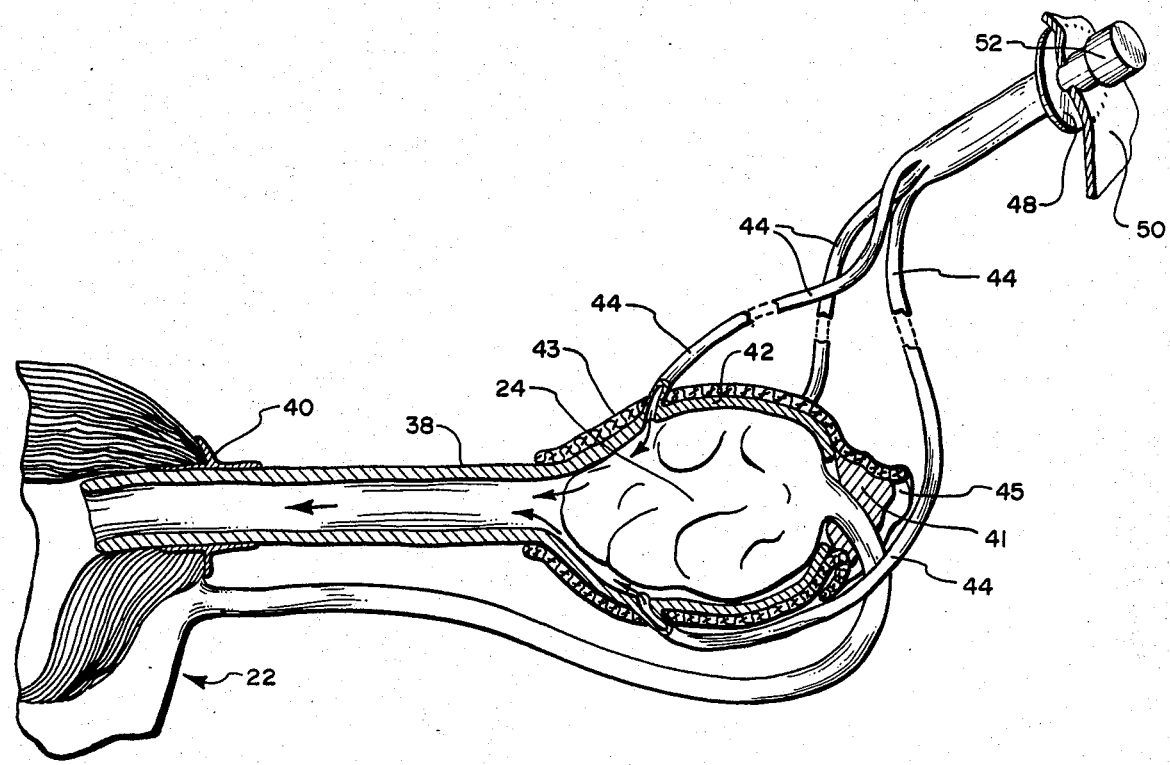
FIG. 5 is a vertical section taken along line 5—5 of FIG. 4, and drawn to a larger scale.

FIG. 3 illustrates a presently preferred embodiment of an artificial fallopian tube in accordance with the present invention. FIGS. 4 and 5 illustrate the manner in which this device is surgically implanted.

Thus, referring to FIGS. 3-5, the apparatus of the present invention advantageously comprises a tubular member 38 capable of carrying an ovum from the ovary to the patient's uterine cavity. As will be better appreciated from the discussion which follows, the inner diameter of tubular member 38 should advantageously be in the range of about 1 millimeter to 2 millimeters, and a length of about 6 centimeters to 8 centimeters. Tubular member 38 should be fabricated from a suitable biocompatible material that will permit a fertilized egg to pass therethrough at a controlled rate without damage and without adhering thereto.

A graft collar 40 is advantageously provided near the distal end of tubular member 38 to facilitate securement of the artificial fallopian tubes to the patient's uterus 22. Graft member 40 may advantageously be formed from a soft material, such as dacron, that is capable of being sutured to uterine tissue. FIG. 5 illustrates that the distal end of tubular member 38 opens into the uterine cavity so that a fertilized egg may be ejected into the uterus for attachment and development.

The proximal end of the tubular member opens into an ovisac 42, which is preferably constructed from a stretchable material that will permit the ovisac to be stretched open to allow placement of ovary 24 therein. The internal diameter of ovisac 42 should be sufficient to retain ovary 24 without binding or otherwise damaging the ovary.

A plurality of nutrient supply tubes 44 are secured to ovisac 42 in a manner that will cause solution introduced through supply tubes 44 to wash the exterior of the ovary so as to carry an ovulated ovum into tubal member 38. Although three supply tubes 44 are illustrated in FIGS. 3-5, it will be appreciated that the exact number of supply tubes 44 and their specific location of attachment on ovisac 42 are subject to substantial variation without losing their function. However, it is important to insure that most of the solution introduced into the artificial fallopian tube travels toward and through tubular member 38 rather than escaping around the proximal end of the ovisac into the patient's peritoneum. One method of preventing reverse flow of nutrient fluid in the artificial fallopian tube is to suture a small piece of omentum 41 around the proximal end of the ovisac to serve as a seal. It is also advantageous to provide ovisac 42 with a cover 43 of dacron or other suitable material to facilitate growth of tissue around the artificial ovisac. Extending this cover proximally advantageously provides a cuff 45 to which an omentum plug may be secured.

In the embodiment illustrated in FIGS. 3-5, three supply tubes are provided, each supply tube being secured at their respective proximal end to an injection member 46. Injection member 46 is provided with a graft member 48 to assist in suturing the injection member to abdominal tissue 50 of the patient. A portion of injection member 46 extends from the patient's abdominal cavity to facilitate introduction of solution into the artificial fallopian tube. When not in use, the injection member may be sealed by use of a removable cap 52, or an appropriate septum, or the like.

After the patient has recovered from surgical implantation of the artificial fallopian tube, ovulation can be induced by intramuscular administration of human chorionic gonadotropin ("HCG"). Ovulation may advantageously be monitored by following the patient'level of luteinizing hormone. Typically, functional ovaries alternate ovulating each sexual cycle. If the patient has a functional ovary in addition to the ovary associated with the artificial fallopian tube, it is advantageous to use ultrasound techniques to observe which ovary is ovulating. When it is determined that the ovary associated with the artificial fallopian tube is near ovulation, a nutrient solution containing sperm is injected through the injection member and into the artificial fallopian tube so as to fill the ovisac with sperm and nutrient solution. Once ovulation occurs, the ovum will be quickly fertilized.

After waiting for up to about twenty-four hours to insure that ovulation has taken place, a microinfusion pump is attached to the proximal end of injection member 46, and nutrient solution is infused into the artificial fallopian tube at a predetermined flow rate. It is preferred that this infusion be conducted in a pulsatile manner (in contrast to a steady flow) in order to decrease any likelihood that the ovum will adhere to the wall of the artificial fallopian tube and to insure that the egg is provided with an adequate supply of fresh nutrient solution, since a pulsatile flow will cause the nutrient solution to advance through the device more rapidly than the egg.

As mentioned above, hormonal changes following ovulation cause changes in the uterine wall that will permit nidation. If a fertilized egg is placed into the uterine cavity too soon or too late, nidation will not occur. Hence, it will be appreciated that the flow rate of nutrient solution and the diameter and length of tubular member 32 are important determinants of the time necessary to transport an egg from ovisac 42 to the distal end of tubular member 38.

In a natural system, as stated above, an egg is ejected from a natural fallopian tube about five to seven days after ovulation. However, it is undesirable to retain the egg in the artificial fallopian tube longer than necessary because of possible damage that can occur to an egg during long periods in an artificial environment. It has been found that nidation is possible if the egg is ejected into the uterine cavity as early as about two to three days after ovulation. It may be desirable to administer progesterone to assist in preparing the uterine cavity for arrival of the fertilized ovum.

Figure 6:
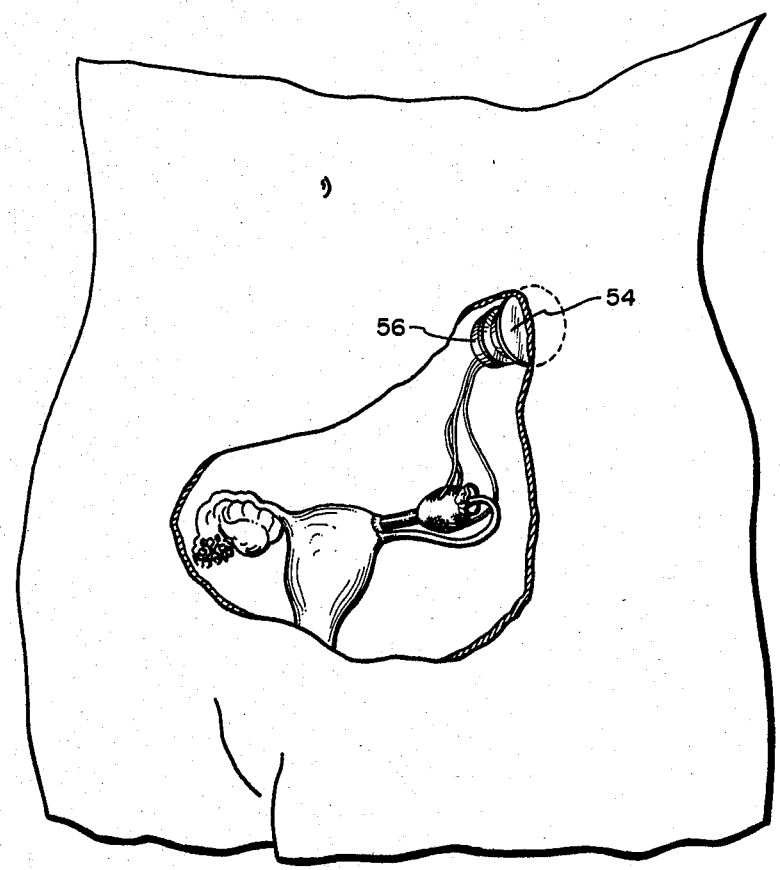
FIG. 6 is a fragmentary view similar to that of FIG. 4, but wherein another presently preferred embodiment of an artificial fallopian tube according to the present invention has been implanted.

A second embodiment of an artificial fallopian tube in accordance with the present invention is illustrated in FIG. 6. In FIG. 6 it may be seen that injection member 46 of the first embodiment may be advantageously replaced by a reservoir 54 and a micropump 56, both of which are implanted in the patient to avoid the need for external attachments and to avoid the need for an opening into the patient's abdomen where infection or irritation may occur. In use, an appropriate solution of nutrients or nutrients plus system is injected through the skin and deposited into reservoir 54. Micropump 56 administers the nutrient solution to the artificial fallopian tube at a desired rate.

In order to more fully appreciate the application of the present invention, a few illustrative examples are presented below. These examples are to be considered in all respects as illustrative and not limiting.

EXAMPLE I

Surgical Implantation of the Artificial Fallopian Tube in a Sheep: The artificial fallopian tube of the present invention may be used in animals as well as humans. This facilitates testing of various parameters of the method and apparatus of the present invention without ethical problems.

In one instance an artificial fallopian tube similar in construction to the embodiment illustrated in FIG. 3 was surgically implanted in a sheep. The sheep was placed under general anesthetic and arranged in the supine position. After making a lower abdominal midline incision, the bowel was packed out of the pelvis to expose the uterus, fallopian tubes, and ovaries for inspection.

Next, the right fallopian tube was excised utilizing cutting current of a cautery instrument. The artificial fallopian tube was introduced into the abdominal cavity, and the artificial ovisac was stretched open to receive the right ovary. The ovisac was then secured by sutures to the mesosalpinx and lateral pelvic wall. The distal end of the artificial fallopian tube was then introduced into the cornual area of the uterus and sutured in place with interrupted sutures.

The injection member was brought out of the abdominal cavity through a stab incision in the right abdominal wall and sutured subcutaneously. After excising the left tube and left ovary the abdominal wall was closed.

EXAMPLES II AND III

Human Implantation: The use of an artificial fallopian according to the present invention is indicated in those cases where a would-be mother has at least one functional ovary, but no functional fallopian tube associated with a functional ovary. If both ovaries are functional and normal, one would be selected for use in association with the artificial fallopian tube.

A human ovary is generally about 2 centimeters wide and about 3 centimeters long. An artificial fallopian tube is advantageously provided with an ovisac about 3 by 4 centimeters, thereby being capable of containing the ovary without constriction. A tubular member interconnecting the ovisac with the patient's uterine cavity is provided having a length of about 6 centimeters, and an inside diameter of about 1 millimeter.

The unused ovary is left in place for possible later use. The ovisac and tubular member are surgically implanted in substantially the same way as set forth in connection with Example I.

In Example II, an artificial fallopian tube similar to the embodiment illustrated in FIGS. 3-5 is provided, and the injection member is brought out of the patient's skin through the abdominal wall at a position suitable to be attached to an infusion pump worn on a belt during periods of use.

In Example III, an artificial fallopian tube similar to the embodiment illustrated in FIG. 6, having an implantable reservoir and pump, is implanted into the patient. The reservoir is positioned subcutaneously so that fluid can be introduced through a syringe. The pump is advantageously programmable by a use of an appropriate radio signal so that it can be turned on and off, and the flow rate regulated. Medtronic, Inc. of Minneapolis, Minn. sells a programmable micropump that is satisfactory for this purpose.

EXAMPLE IV

A patient fitted with an artificial fallopian tube as set forth in Example III is given an intramuscular injection of human chorionic gonadotropin to induce ovulation. As ovulation approaches, an ultrasound image is taken to determine whether the ovary associated with the artificial fallopian tube is approaching ovulation. In the event the unassociated ovary is found to be ovulating, the procedure is terminated until the following month.

Where the ovary associated with the artificial fallopian tube is in the process of ovulating, the condition of the ovary is monitored by following an increase in the blood level of luteinizing hormone. As the level of luteinizing hormone increases to about double the normal baseline level, a specimen of fresh seminal fluid is obtained from the prospective father, or a frozen specimen of seminal fluid is thawed. The sperm contained in the seminal fluid is separated from the other seminal fluid constituents, and mixed with nutrient media in a concentration of about 200,000 motile sperm per cubic centimeter of nutrient media. The mixture of nutrient solution and sperm is then loaded into the reservoir of the artificial fallopian tube, after which the micropump is activated at a relatively high flow rate to effectively charge the ovisac with sperm and nutrients. The micropump is then deactivated.

Upon ovulation, the high concentration of sperm within the ovisac will generally insure rapid fertilization. It is advantageous to leave the spermal nutrient solution and ovum undisturbed for several hours at this point to insure that fertilization has an opportunity to occur, and to minimize any possibility of trauma to the ovum before it has an opportunity to commence cellular development.

After a suitable period of time, the reservoir is recharged with nutrient solution and the micropump is programmed to continuously pump a small amount of fluid into the ovisac in a pulsatile manner. Solution will be forced out of the distal end of the tubular member of the artificial fallopian tube, so that the ovum will be carried into and through the tubular member.

The use of pulsatile flow is advantageous because the regular pulsing of fluid helps insure that the ovum receives an adequate supply of nutrient. If a steady flow of nutrient solution is introduced into the device, the egg will travel through the artificial fallopian tube at substantially the same rate as the nutrient solution. Under these conditions, essential nutrients will become depleted in the region around the ovum. In contrast, if nutrient solution is introduced in a pulsatile manner, nutrient solution will rush past the ovum before the ovum commences accelerating, thereby assuring that the ovum is regularly provided with fresh nutrients. The use of pulsatile flow also assists to prevent the ovum from adhering to the material of the artificial fallopian tube because each pulse provides a relatively high pressure charge of fluid.

The micropump should be programmed to pump an appropriate volume of fluid that will cause the ovum to pass through the artificial fallopian tube and into the patient's uterus approximately two to three days after ovulation, a time when the uterus is prepared for nidation. Optionally, the patient is administered an intramuscular dose of progesterone immediately following ovulation, and again for the next two days; some researchers believe this regimen will assist in preparing the uterus for nidation.

From the foregoing, it will be appreciated that the present invention provides a practical alternative to in vitro fertilization in patients having dysfunctional natural fallopian tubes.

Further, unlike the in vitro technique which subjects the patient to repeated hospital stays and surgical operations, and requires a substantial amount of attention by surgical and laboratory personnel, the methods and apparatus of the present invention are relatively burden-free and permit the patient to live a relatively normal life during the period when ovulation occurs. Multiple attempts to induce pregnancy may be made with relative ease, and multiple pregnancies are possible without the need for additional surgery.

Although the methods and apparatus of the present invention have been shown and described with reference to particular embodiments, it is to be understood that the apparatus of the invention may also be embodied in other specific forms without parting from the spirit or essential characteristics of the present invention. The described embodiments are to be considered in all respects as illustrative and not restrictive. The scope of the invention is, therefore, indicated by the appended claims rather than by the foregoing description. All changes which come within the meaning and range of equivalency are to be embraced within their scope.

What is claimed and desired to be secured by United States Letters Patent is:

1. A prosthetic fallopian tube adapted for surgical placement in a patient lacking functional natural fallopian tubes, comprising:
    means for collecting ova discharged by one of the patient's ovaries;
    means for communicating between the collecting means and the patient's uterine cavity so that ova collected by the collecting means can pass into the uterine cavity;
    means for carrying fluid into the collecting means such that ova collected by the collecting means will be carried from the collecting means to the uterine cavity; and
    means for controlling the rate that fluid is carried into the collecting means so that the ovum is ejected into the uterine cavity at a time when nidation is possible.

2. A prosthetic fallopian tube as defined in claim 1, wherein the collecting means comprises ovisac means for encapsulating the patient's ovary.

3. A prosthetic fallopian tube as defined in claim 2, wherein the ovisac means is shaped to fit closely about the ovary, said ovisac means being fabricated from a material capable of being stretched sufficiently to permit placement to the ovary therein without causing injury to said ovary.

4. A prosthetic fallopian tube as defined in claim 1, wherein the communicating means comprises tubular means having a proximal end communicating with the collecting means and a distal end adapted for surgical attachment in communication with the uterine cavity.

5. A prosthetic fallopian tube as defined in claim 4, wherein the tubular means has a diameter suitable to permit a fertilized egg to pass therethrough at a controlled rate.

6. A prosthetic fallopian tube as defined in claim 1, wherein the means for carrying fluid into the collecting means comprises a plurality of fluid supply tubes.

7. A prosthetic fallopian tube as defined in claim 2, wherein the means for carrying fluid into the collecting means comprises a plurality of fluid supply tubes secured at spaced positions about and in communication with the ovisac means.

8. A prosthetic fallopian tube as defined in claim 1, wherein the controlling means comprises pump means adapted to introduce fluid into the carrying means in a pulsatile manner.

9. A prosthetic fallopian tube as defined in claim 7, wherein the controlling means comprises pump means adapted to introduce fluid into the carrying means in a pulsatile manner.

10. A prosthetic fallopian tube as defined in claim 1, further comprising reservoir means into which fluid is placed, and wherein the fluid carried into the collecting means by the carrying means is obtained from said reservoir means.

11. A prosthetic fallopian tube as defined in claim 10, wherein the reservoir means is adapted to be implanted beneath the patient's skin.

12. A prosthetic fallopian tube as defined in claim 9, further comprising reservoir means into which fluid is placed, and wherein the pump means pumps fluid from the reservoir means into the supply tubes.

13. A prosthetic fallopian tube as defined in claim 12, wherein the reservoir means and the pump means are adapted to be implanted in the patient.

14. A prosthetic fallopian tube adapted for surgical placement in a patient lacking functional natural fallopian tubes, comprising:
 ovisac means for encapsulating one of the patient's ovaries in order to collect ova discharged from said ovary;
 tubular means having a proximal end communicating with the ovisac means and a distal end adapted for surgical attachment in communication with the uterine cavity, said tubular means having a suitable diameter to permit a fertilized ovum to pass therethrough;
 means for carrying fluid into the ovisac means such that ova discharged from the ovary will be carried from the collecting means towards the uterine cavity; and
 means for introducing fluid into the carrying means in a pulsatile manner and at a rate such that a fertilized ovum arrives at the distal end of the tubular means and is ejected into the uterine cavity as a time when nidation is possible.

15. A prosthetic fallopian tube as defined in claim 14, wherein the means for carrying fluid into the ovisac means comprises a plurality of fluid supply tubes secured at spaced positions about and in communication with the ovisac means.

16. A prosthetic fallopian tube as defined in claim 15, further comprising reservoir means to hold fluid to be introduced into the fluid supply tubes.

17. A prosthetic fallopian tube as defined in claim 16, wherein the introducing means comprises pump means adapted to introduce fluid into the fluid supply tubes in a pulsatile manner.

18. A prosthetic fallopian tube as defined in claim 17, wherein the pump means and the reservoir means are adapted to be surgically implanted in the patient.

19. A method for collecting and fertilizing an ovum and introducing the fertilized ovum into the uterus of a patient having dysfunctional fallopian tubes at a time suitable for nidation comprising the steps of:
 implanting an artificial fallopian tube including means for collecting an ovum discharged from one of the patient's ovaries, means for introducing fluid into the artificial fallopian tube, and means for ejecting the ovum into the patient's uterine cavity;
 introducing a fluid including nutrients and sperm into the artificial fallopian tube;
 ejecting the ovum into the uterine cavity at a time when nidation is possible.

20. A method for collecting and fertilizing an ovum and introducing the fertilized ovum into the uterus of a patient as defined in claim 19 wherein the fluid including nutrients and sperm is introduced into the artificial fallopian tube a suitable period of time prior to ovulation and is left in place for a suitable period of time following ovulation in order to cause fertilization of the ovum discharged from the ovary.

21. A method for collecting and fertilizing an ovum and introducing the fertilized ovum into the uterus of a patient as defined in claim 19 comprising the further step of introducing additional fluid containing nutrients into the artificial fallopian tube following fertilization so as to nourish the fertilized ovum and to cause said ovum to move towards the uterine cavity at a controlled rate that will result in ejecting the fertilized ovum into the uterine cavity at a time when nidation is possible.

22. A method for collecting and fertilizing an ovum and introducing the fertilized ovum into the uterus of a patient as defined in claim 21, wherein the step of introducing additional fluid into the collecting means of the artificial fallopian tube following fertilization is performed in a continuous pulsatile manner.

23. A method for collecting and fertilizing an ovum and introducing the fertilized ovum into the uterus of a patient having dysfunctional fallopian tubes at a time suitable for nidation comprising the steps of:
 implanting an artificial fallopian tube including means for collecting an ovum discharged from one of the patient's ovaries, means for introducing fluid into the artificial fallopian tube, and tubular means for carrying the ovum into the uterine cavity;
 introducing fluid containing sperm and nutrients into the artificial fallopian tube a suitable period prior to ovulation;
 waiting a suitable period for ovulation and fertilization to occur;
 introducing fluid containing nutrients into the artificial fallopian tube in a continuous pulsatile manner to cause the ovum to advance towards the uterine cavity at a controlled rate until the ovum is ejected into the uterine cavity at a time when nidation is possible.

* * * * *

UNITED STATES PATENT AND TRADEMARK OFFICE
CERTIFICATE OF CORRECTION

PATENT NO. : 4,574,000

DATED : March 4, 1986

INVENTOR(S) : Stephen K. Hunter

It is certified that error appears in the above-identified patent and that said Letters Patent is hereby corrected as shown below:

```
Column 4, line 1,  "hundred" should be --hundreds--
Column 4, line 42, "tubes" should be --tube--
Column 4, line 59, "tubal" should be --tubular--
Column 9, line 5,  "to the" should be --of the--
Column 9, line 64, "as a" should be --at a--
```

Signed and Sealed this

Seventeenth Day of June 1986

[SEAL]

Attest:

DONALD J. QUIGG

*Attesting Officer*      *Commissioner of Patents and Trademarks*